US012433809B2

(12) United States Patent
Grabow

(10) Patent No.: US 12,433,809 B2
(45) Date of Patent: Oct. 7, 2025

(54) HAND TABLE DEVICE FOR SURGEONS

(71) Applicant: Ryan Grabow, Henderson, NV (US)

(72) Inventor: Ryan Grabow, Henderson, NV (US)

(*) Notice: Subject to any disclaimer, the term of this patent is extended or adjusted under 35 U.S.C. 154(b) by 1245 days.

(21) Appl. No.: 16/951,499

(22) Filed: Nov. 18, 2020

(65) Prior Publication Data

US 2021/0145682 A1 May 20, 2021

Related U.S. Application Data

(60) Provisional application No. 62/938,181, filed on Nov. 20, 2019.

(51) Int. Cl.

*A61G 13/00* (2006.01)
*A61B 17/02* (2006.01)
*A61F 5/01* (2006.01)
*A61G 13/10* (2006.01)
*A61G 13/12* (2006.01)

(52) U.S. Cl.

CPC .......... *A61G 13/0045* (2016.11); *A61B 17/02* (2013.01); *A61F 5/0118* (2013.01); *A61G 13/101* (2013.01); *A61G 13/124* (2013.01)

(58) Field of Classification Search

CPC .............. A61G 13/0045; A61G 13/101; A61G 13/124; A61F 5/0118; A61B 17/02; A61B 17/0206; A61B 17/0212; A61B 90/57

USPC ........... 5/646, 647; 602/20, 21, 64; 128/878, 128/879

See application file for complete search history.

(56) References Cited

U.S. PATENT DOCUMENTS 3,746,332 A * 7/1973 Hakstian .............. A61G 13/124 5/647
4,082,257 A * 4/1978 Strickland .......... A61G 13/0045 5/606
4,807,864 A * 2/1989 Young ................ A61G 13/0045 5/617
4,941,480 A * 7/1990 McLean .............. A61F 5/05841 128/878
5,060,638 A * 10/1991 Bodine, Jr. ........... A61F 5/3761 128/845

(Continued)

FOREIGN PATENT DOCUMENTS

CN 108784849 A * 11/2018
WO 2020106196 A1 5/2020

OTHER PUBLICATIONS

Translation of CN-108784849-A.*
International Search Report and Written Opinion dated Apr. 28, 2021 for PCT Application No. PCT/US20/61095, 9 pages.

*Primary Examiner* — David R Hare
(74) *Attorney, Agent, or Firm* — FisherBroyles, LLP; Rob L. Phillips

(57) ABSTRACT

Hand table device for surgeons including a rectangular, rigid platform having elevated edges running along each long side thereof. The elevated edges allow the surgeon and assistant to rest their arms/wrists to prevent fatigue of their arms and shoulders while also providing a solid foundation for the surgeon's arms/wrists during a delicate procedure. The edges further prevent instruments and fluids from exiting the surgery area. The rigid platform may include magnets which, along with secondary metallic articles, permit instruments, medical devices and a patient's body part to be secured or immobilized as needed. The hand table device may be disposable for one-time use only.

14 Claims, 10 Drawing Sheets

(56) References Cited

U.S. PATENT DOCUMENTS

| | | | | | |
|---|---|---|---|---|---|
| 5,074,291 | A * | 12/1991 | Carter | A61G 13/0045 | 606/241 |
| 5,097,963 | A * | 3/1992 | Chernosky | A61B 50/20 | D24/227 |
| 5,140,998 | A * | 8/1992 | Vickers | A61G 13/0045 | 128/880 |
| 5,372,145 | A * | 12/1994 | Berger | A61G 13/0045 | 602/20 |
| 5,547,463 | A * | 8/1996 | Hinchliffe | A61B 90/00 | 600/102 |
| 5,881,730 | A * | 3/1999 | Burger | A61G 13/12 | 602/20 |
| 6,824,511 | B1 * | 11/2004 | Bell | A61B 17/02 | 600/227 |
| 11,963,912 | B2 * | 4/2024 | Lewold | A61G 13/124 | |
| 2004/0186356 | A1 * | 9/2004 | O'Malley | A61B 17/02 | 600/231 |
| 2006/0272979 | A1 * | 12/2006 | Lubbers | A61B 17/02 | 206/557 |
| 2018/0055708 | A1 * | 3/2018 | Hatch | A61G 13/124 | |
| 2019/0159843 | A1 | 5/2019 | Demri et al. | | |
| 2019/0201162 | A1 * | 7/2019 | Thomas | A61B 90/57 | |
| 2020/0206010 | A1 * | 7/2020 | Du | A61F 5/05841 | |

* cited by examiner

HAND TABLE DEVICE FOR SURGEONS

This application claims the benefit of U.S. Ser. No. 62/938,181 filed on Nov. 20, 2019 which is incorporated herein for all purposes.

FIELD OF THE INVENTION

Field of the Invention

The embodiments of the present invention relate to a hand table device for surgeons (e.g., hand surgeons and orthopedic surgeons) to use during surgery in the operating room or office procedure room.

Background

Conducting intricate surgery in an operating room or office location is a challenging exercise. One issue faced by surgeons and their assistants is their hand placement and fatigue. Another issue is preventing instruments and medical devices from falling off the table. Yet another issue is securing the body part (e.g., hand, wrist) being repaired. Another issue is the need for tissue retraction to undertake the surgery. Another issue is the number of persons needed to assistant in the surgery. Another issue is maintaining retraction when the assistant needs to use their hands for other tasks.

It would be advantageous to develop a hand table device to overcome the issues facing surgeons including surgeon and assistant hand placement, surgeon and assistant hand fatigue, instrument and medical device security from falling off the table, body part positioning on the table, tissue retraction, and persons needed to undertake a surgery.

SUMMARY

Accordingly, one embodiment of the present invention is a hand table device for surgeons comprising a rectangular, rigid platform having elevated edges running along each long side thereof. The elevated edges allow the surgeon and assistant to rest their arms/wrists in an ergonomic position to prevent fatigue of their arms and shoulders while also providing a solid foundation for the surgeon's arms/wrists during a delicate procedure. The edges further prevent instruments and fluids from exiting the surgery area.

In one embodiment, the rigid platform includes magnets which, along with secondary metallic articles, permit instruments, medical devices and a patient's body part to be secured or immobilized as needed. In one embodiment, the hand table device elevated supports are disposable and intended for one-time use only.

Other variations, embodiments and features of the present invention will become evident from the following detailed description, drawings and claims.

DETAILED DESCRIPTION

Figure 1:
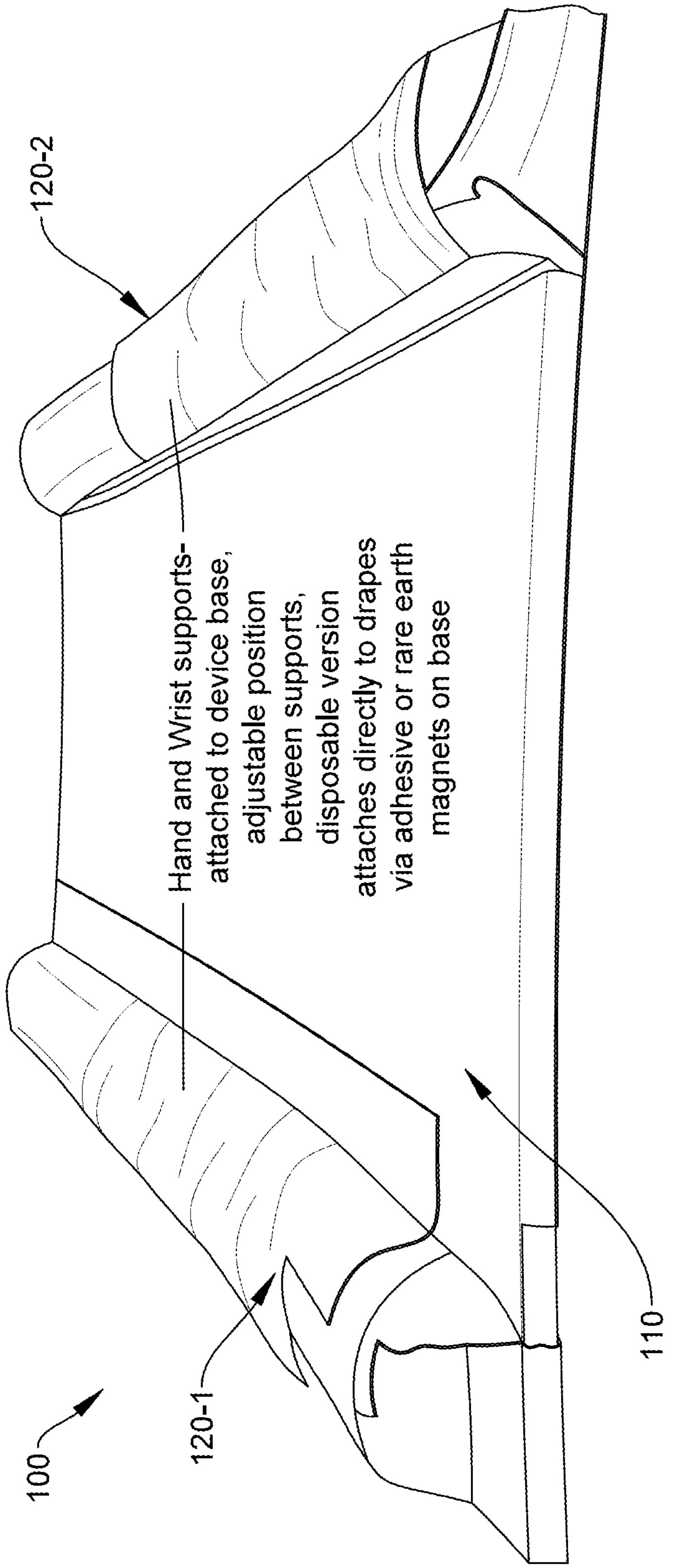
FIG. 1 illustrates an end view of a hand table device according to the embodiments of the present invention.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

In one embodiment, the hand table device detailed herein fabricated of rubber, silicone and/or dense foam. Those skilled in the art will understand that other materials may be used without departing from the spirit and scope of the present invention. The hand table device is configured to achieve numerous objectives including (i) providing a barrier to prevent instruments from falling off the hand table during surgery; (ii) providing a barrier to irrigation fluid or bodily fluids from spilling onto the surgeon or surgical assistant's lap or feet during a procedure; (iii) securing hand table drape firmly in position to avoid sliding and contamination; (iv) supporting the surgeon's and surgical assistant's wrists/forearms while working to reduce shoulder and arm fatigue; (v) supporting the surgeon's and surgical assistant's wrists to enhance their hand stability during delicate maneuvers; (vi) securing surgical retraction instruments in position (via magnets) to free up the surgical assistant's hands for other maneuvers; (vii) securing surgical retraction instruments in position (via magnets) to enable the surgeon to operate without a surgical assistant; and (viii) securing patient's hands/fingers in position while surgeon is operating. The hand table device is further adaptable for use with any commercial hand table, mayo stand, or support in the operating room and/or any desk, table, or arm procedure support in an office setting.

Figure 2:
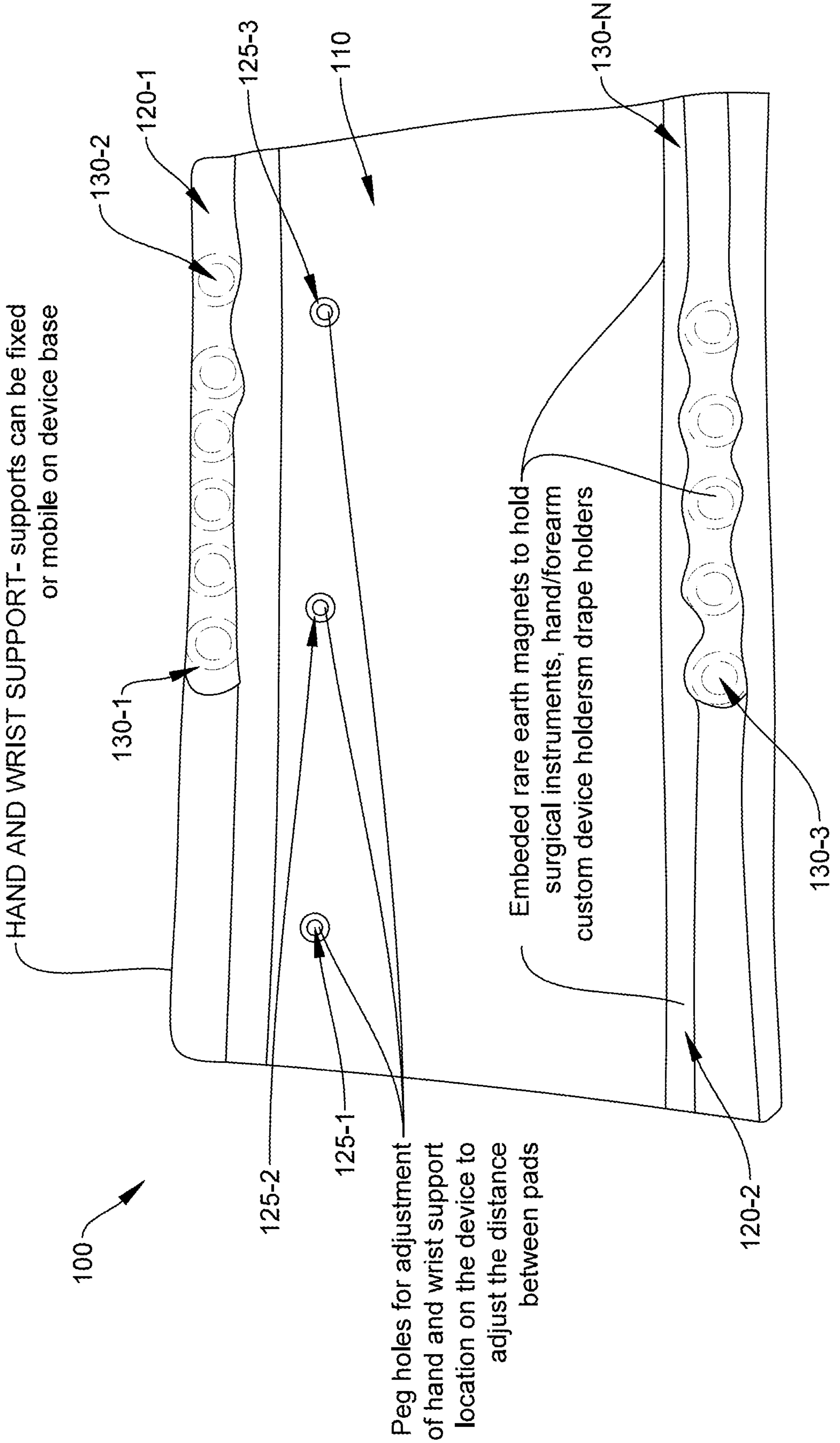
FIG. 2 illustrates a top down view of the hand table device according to the embodiments of the present invention.

As shown in FIGS. 1-2, the hand table device 100 comprises broadly a rectangular platform 110 with elevated edges 120-1, 120-2 along its long sides or at least one of its sides. The platform may take on any number of shapes. In one embodiment, the elevated edges 120-1, 120-2 are semicircular in cross-section but other cross-sections may be used. The elevated edges 120-1, 120-2 serve numerous purposes as detailed below. First, the elevated edges 120-1, 120-2 act as physical barriers to prevent instruments, medical devices (e.g., implants) and other surgical necessities, as well as irrigation and bodily fluids, from inadvertently falling and leaking off the surgical area requiring re-sterilization or clean up. The elevated edges 120-1, 120-2 also provide a resting place for the surgeon's wrists and forearms (and surgeon's assistant's wrists and forearms) as needed. Resting the wrists and forearms prevents fatigue to the surgeon's and assistant's arms and shoulders and further provides a stable location for the surgeon to position wrists or forearms for delicate surgical procedures.

In one embodiment, at least one of the elevated edges 120-1, 120-2 may be re-positioned on the platform 110. As shown in FIG. 2, elevated edge 120-1 may be repositioned using the holes 125-1 through 125-3 on the platform 110. In this embodiment, pegs (not shown) extending from a bottom of elevated edge 120-1 are inserted into the holes 125-1 through 125-3 on the platform 110 securing the repositioned elevated edge 120-1. Other means, including magnets, snaps, hook and hook fasteners and the like may be used to secure the repositioned elevated edge 120-1.

Figure 4:
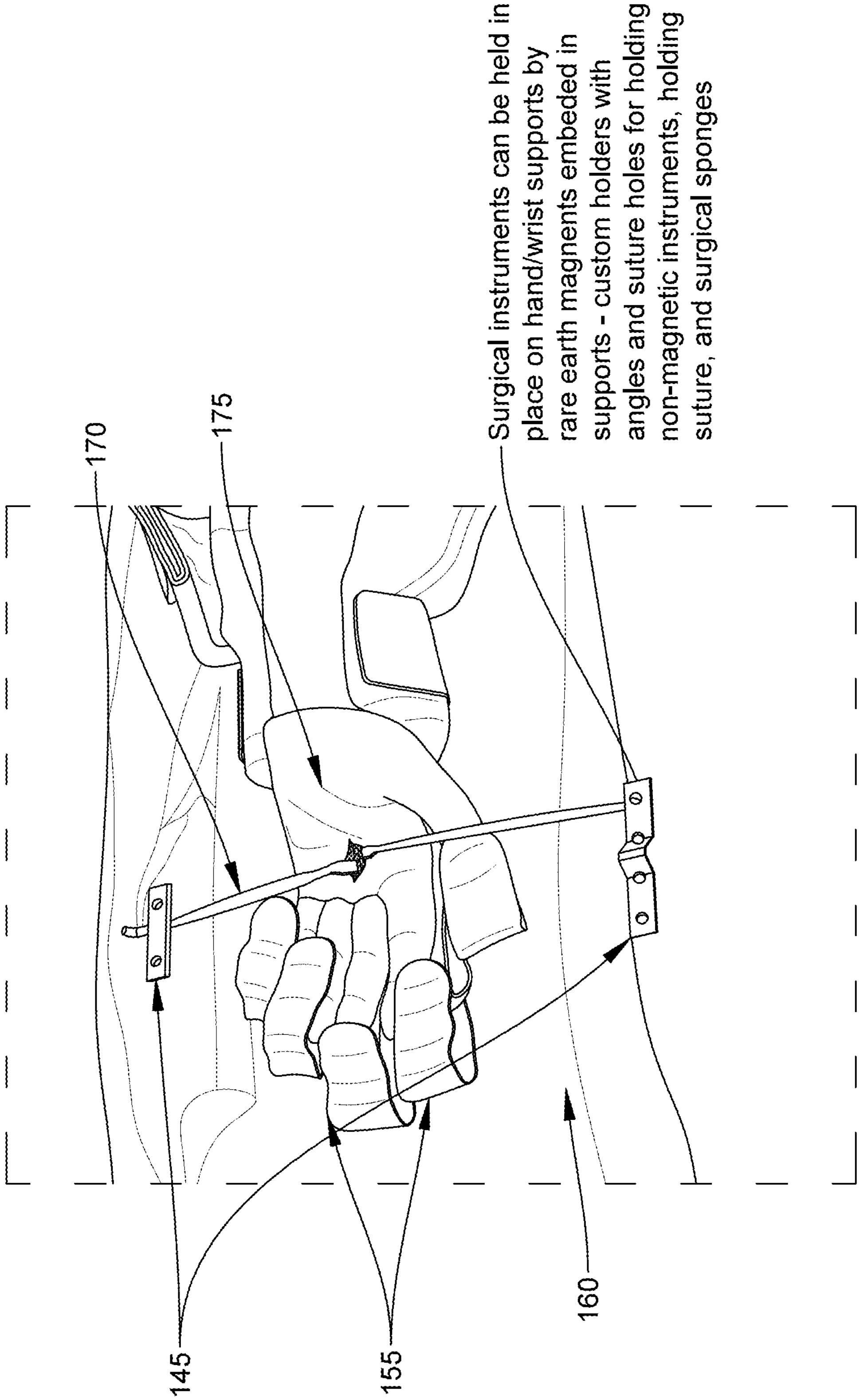
FIG. 4 illustrates a patient's hand secured to the hand table device and an incision being held open according to the embodiments of the present invention.

In one embodiment, each elevated edge 120-1, 120-2 incorporates magnets 130-1 through 130-N (e.g., rare earth magnets). The magnets 130-1 through 130-N can be integrated into the elevated edges 120-1, 120-2 during fabrication or the elevated edges 130-1 through 130-N may come with slots or similar features allowing the surgeon to customize the placement of the magnets for purposes disclosed below. Regardless of the embodiment, as shown in FIGS. 4-6, the magnets 130-1 through 130-N serve to (i) secure a surgical drape to the hand table device 100, (ii) secure surgical retraction instruments in place and (iii) secure the body part (e.g., hand) in place.

Figure 3:
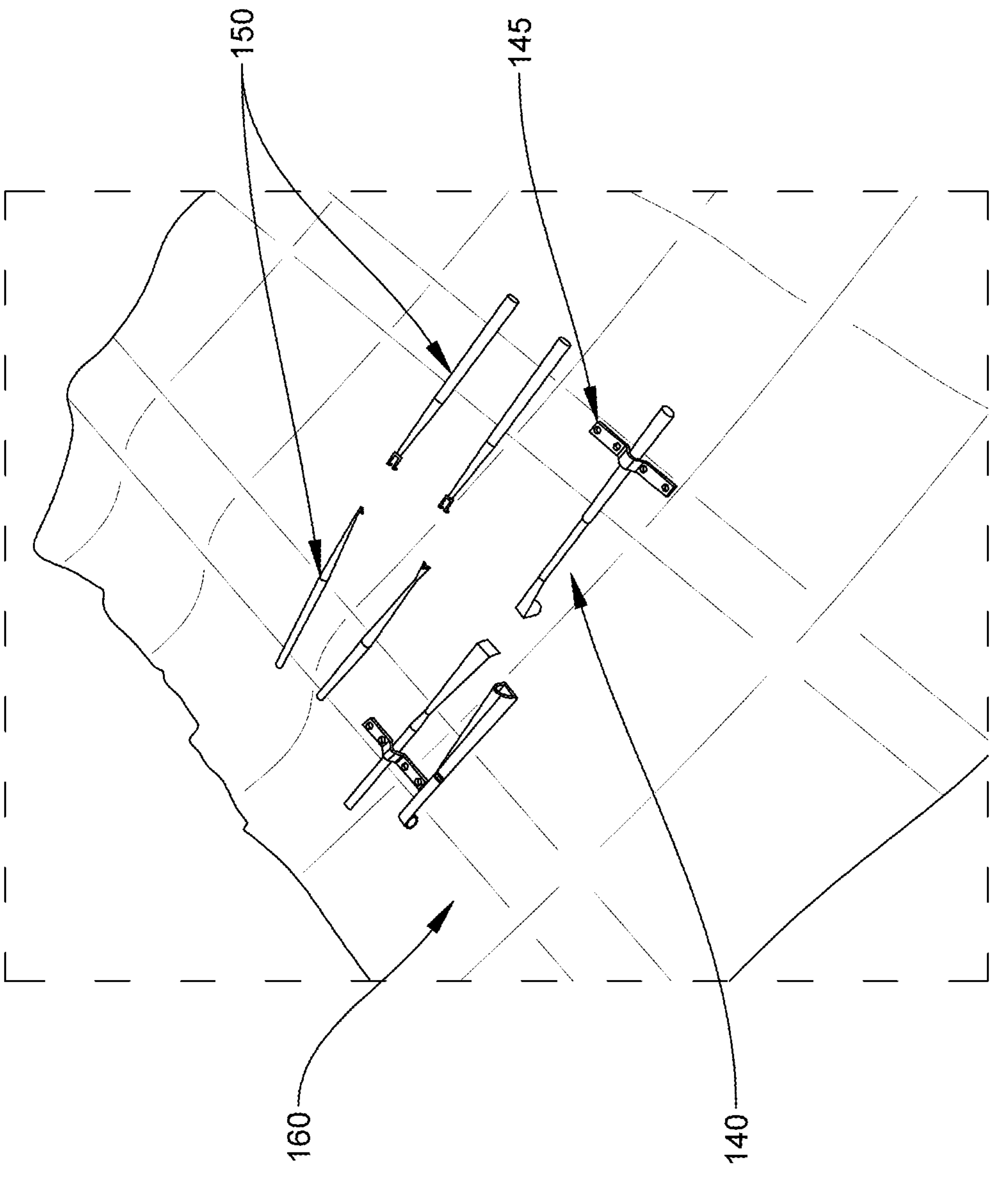
FIG. 3 illustrates the hand table device with a surgical drape in place and medical devices and instruments held in place according to the embodiments of the present invention.

FIG. 3 shows non-magnetic instruments 140 and magnetic instruments 150 held in place via magnets 130-1 through 130-N. Magnetic instruments 150 are simply held in place by being positioned proximate the magnets 130-1 through 130-N in the elevated edges 120-1, 120-2. Magnetic clips 145 are used to secure the non-magnetic instruments 140 to the hand table device 100. The attraction between the magnets 130-1 through 130-N and the magnetic instruments 150 and magnetic clips 145 also serves to maintain a surgical drape 160 in place over the hand table device 100. In an alternative embodiment, the surgical drape 160 may incorporate magnetic members positioned to attract to one or more of the magnets 130-1 through 130-N to maintain the surgical drape 160 in place.

Figure 5:
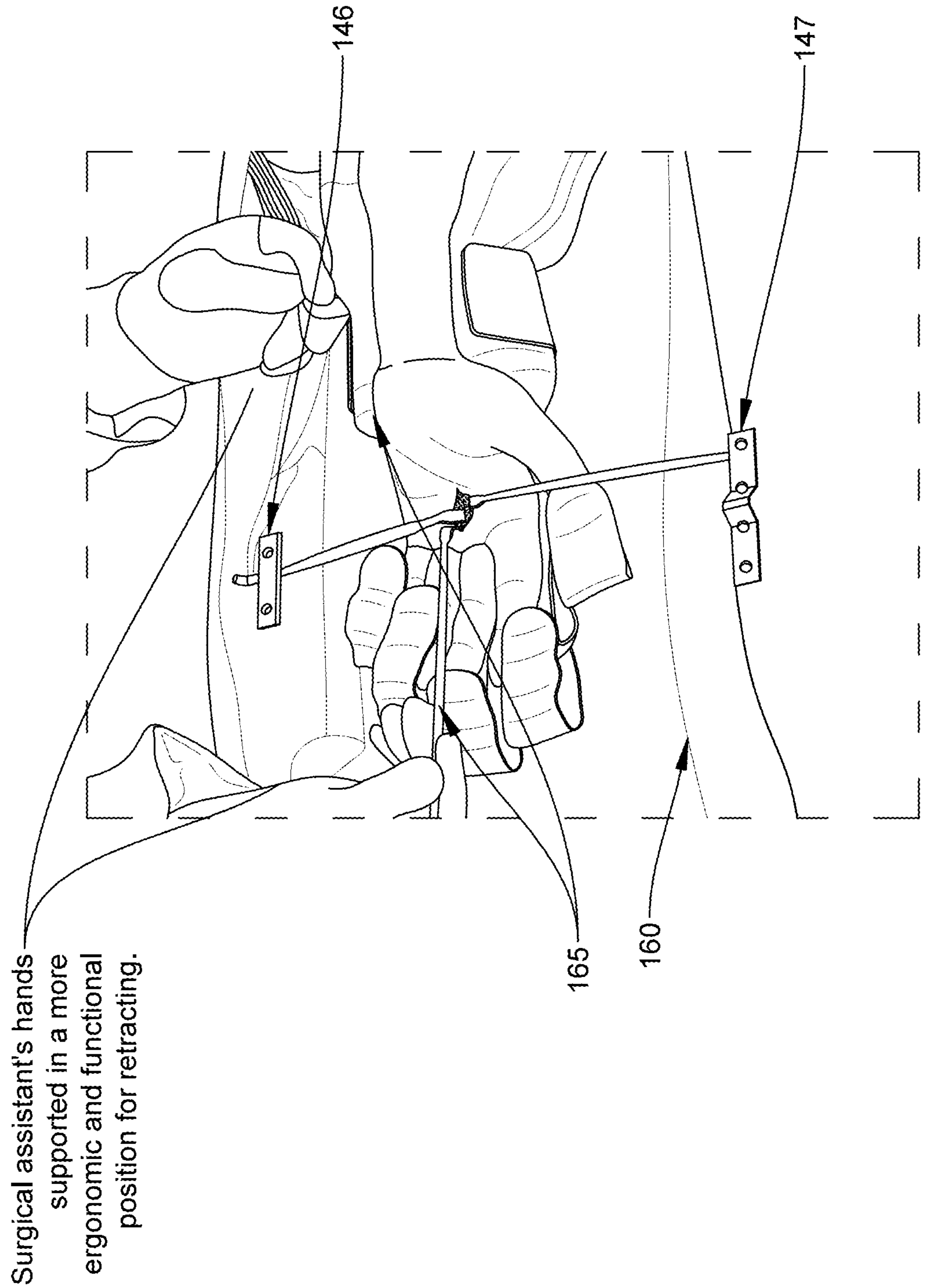
FIG. 5 illustrates a patient's hand secured to the hand table device and an incision being held open while a medical assistant retracts according to the embodiments of the present invention.

Now referring to FIGS. 4-7, surgical retraction instruments 170 are held in place via the magnets 130-1 through 130-N and magnetic clips 145. As shown, the magnetic clips 145 may hold the instruments in place in multiple ways (e.g., downward pressure 146, openings 147). A hand 175 being operated upon is secured via magnets positioned in the platform 110 of the hand table device 100 and magnetic finger clips 155. FIG. 5 shows a doctor's assistant retracting the incision with instruments 165 while the retraction instruments 170, held in place by the magnets 130-1 through 130-N, also do so.

Figure 6:
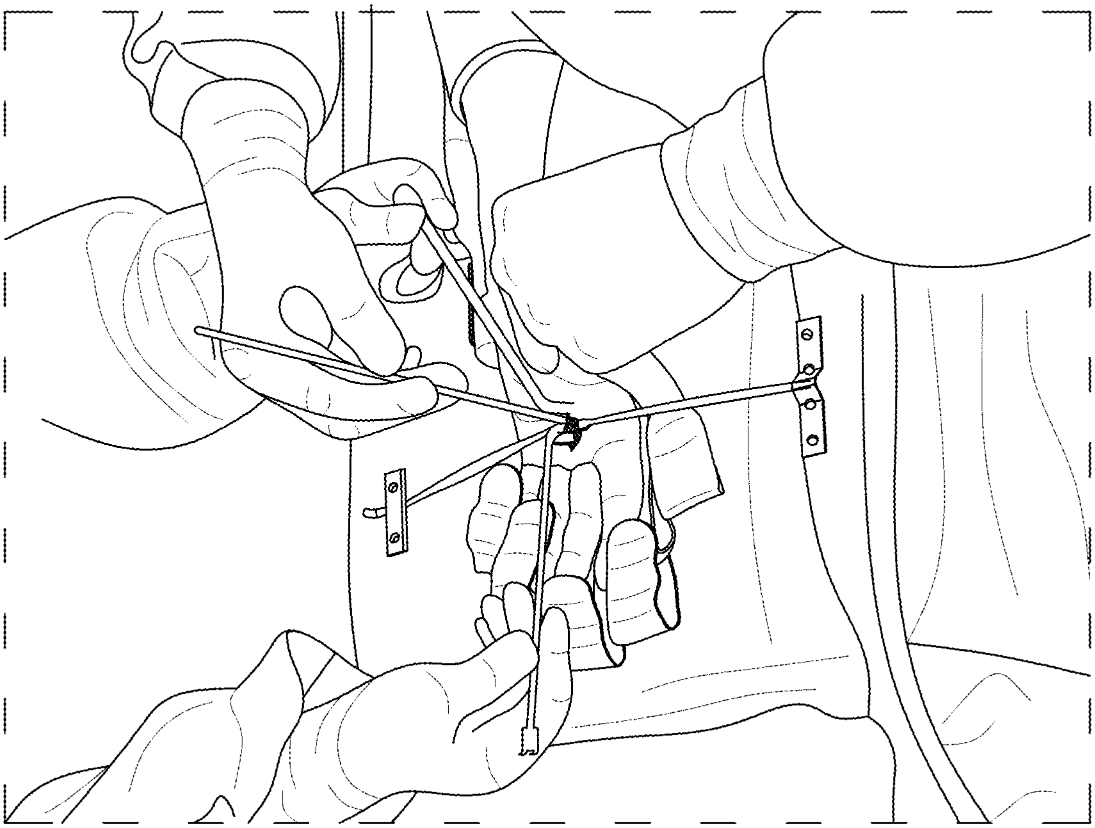
FIG. 6 illustrates a patient's hand secured to the hand table device and an incision being held open while a medical assistant retracts the incision, and a surgeon operates according to the embodiments of the present invention.

FIG. 6 shows the patient's hand 175 secured to the hand table device 100 and an incision being held open while a medical assistant retracts the incision and a surgeon operates according to the embodiments of the present invention.

Figure 7:
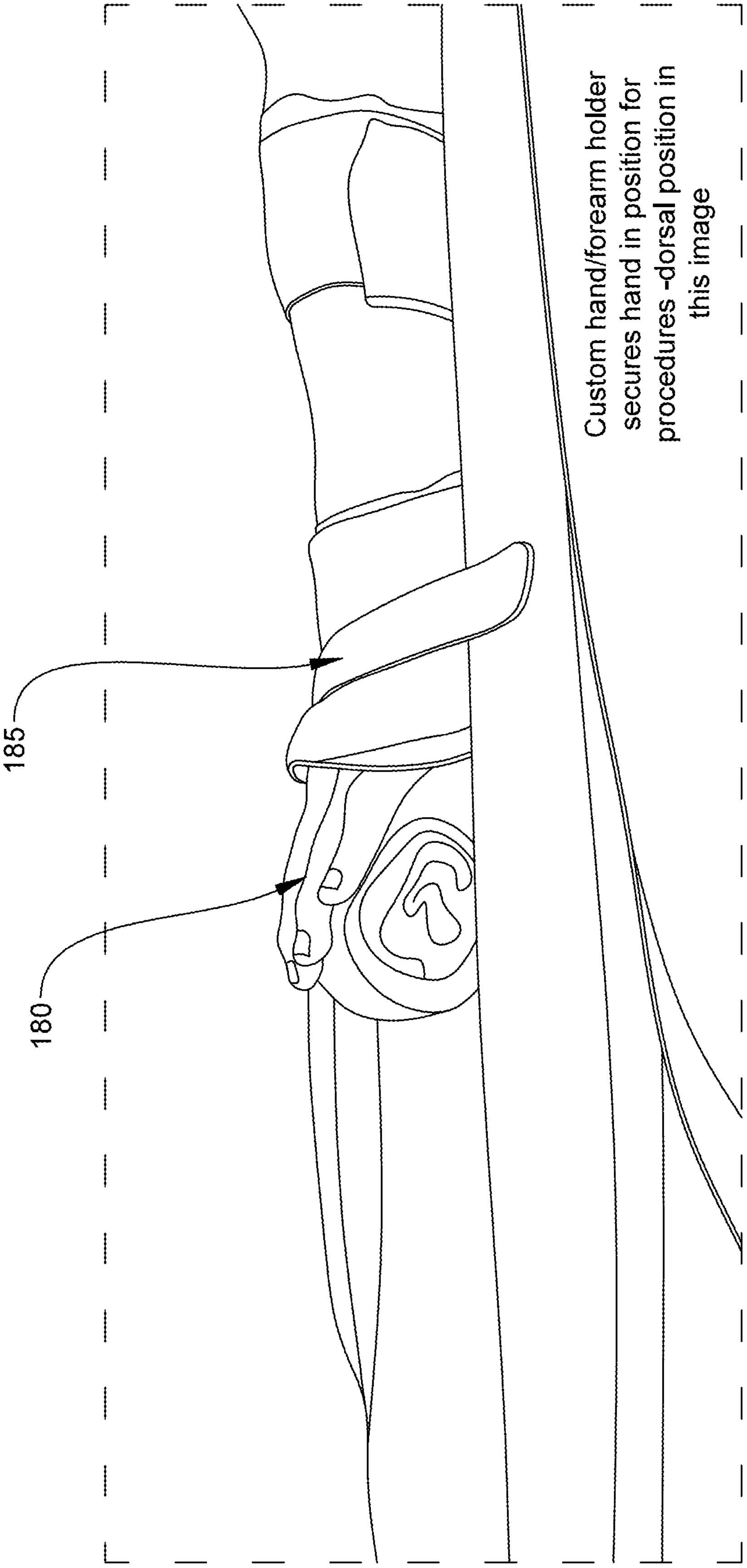
FIG. 7 illustrates a patient's hand secured to the hand table device via a slat member according to the embodiments of the present invention.
Figure 8:
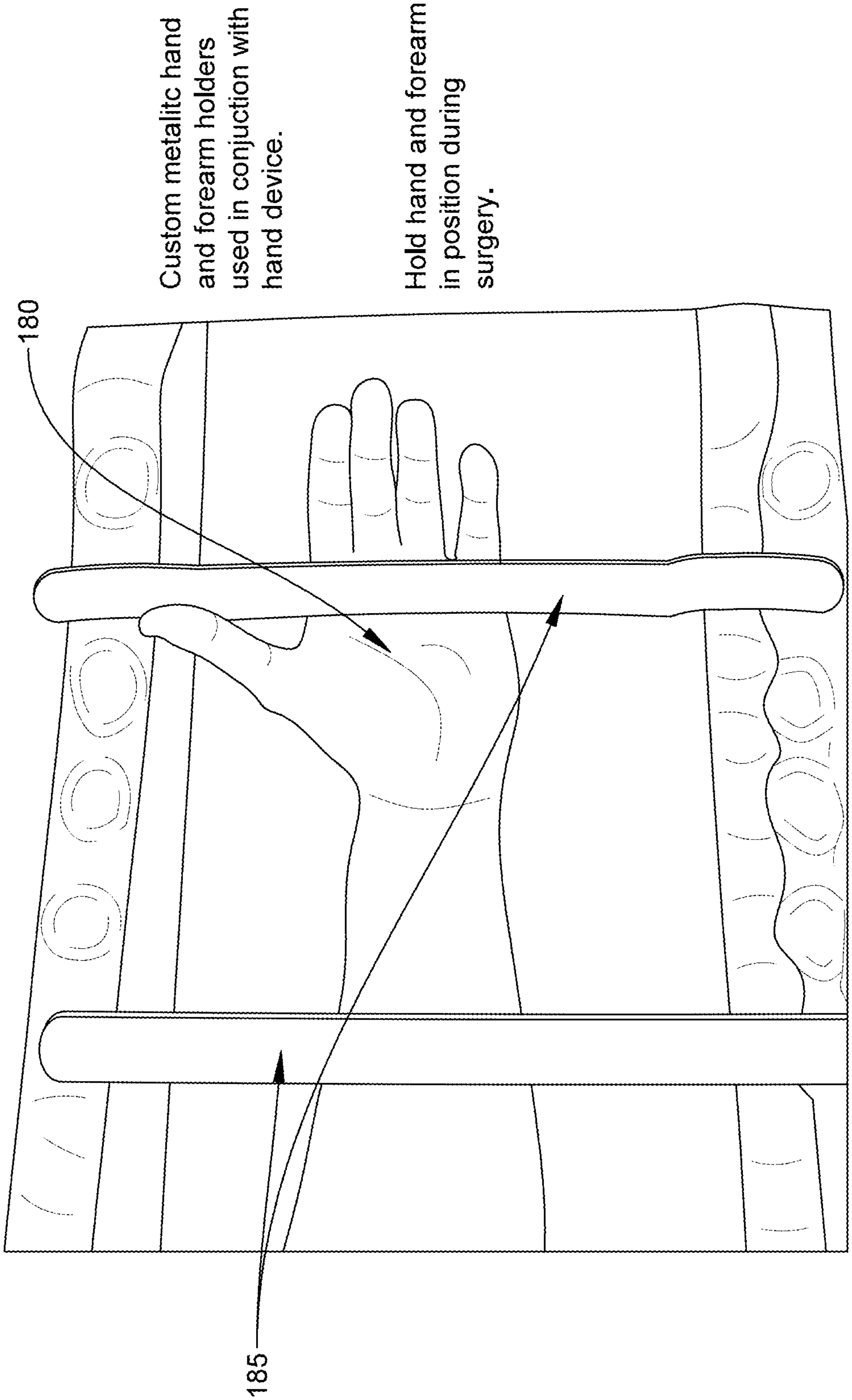
FIG. 8 illustrates a patient's hand secured to the hand table device via a pair of slat members according to the embodiments of the present invention.

FIG. 7 shows a patient's hand 180 secured to the hand table device 100 via a slat member 185 according to the embodiments of the present invention and FIG. 8 shows the patient's hand 180 secured to the hand table device 100 via a pair of slat members 185 according to the embodiments of the present invention.

Figure 9:
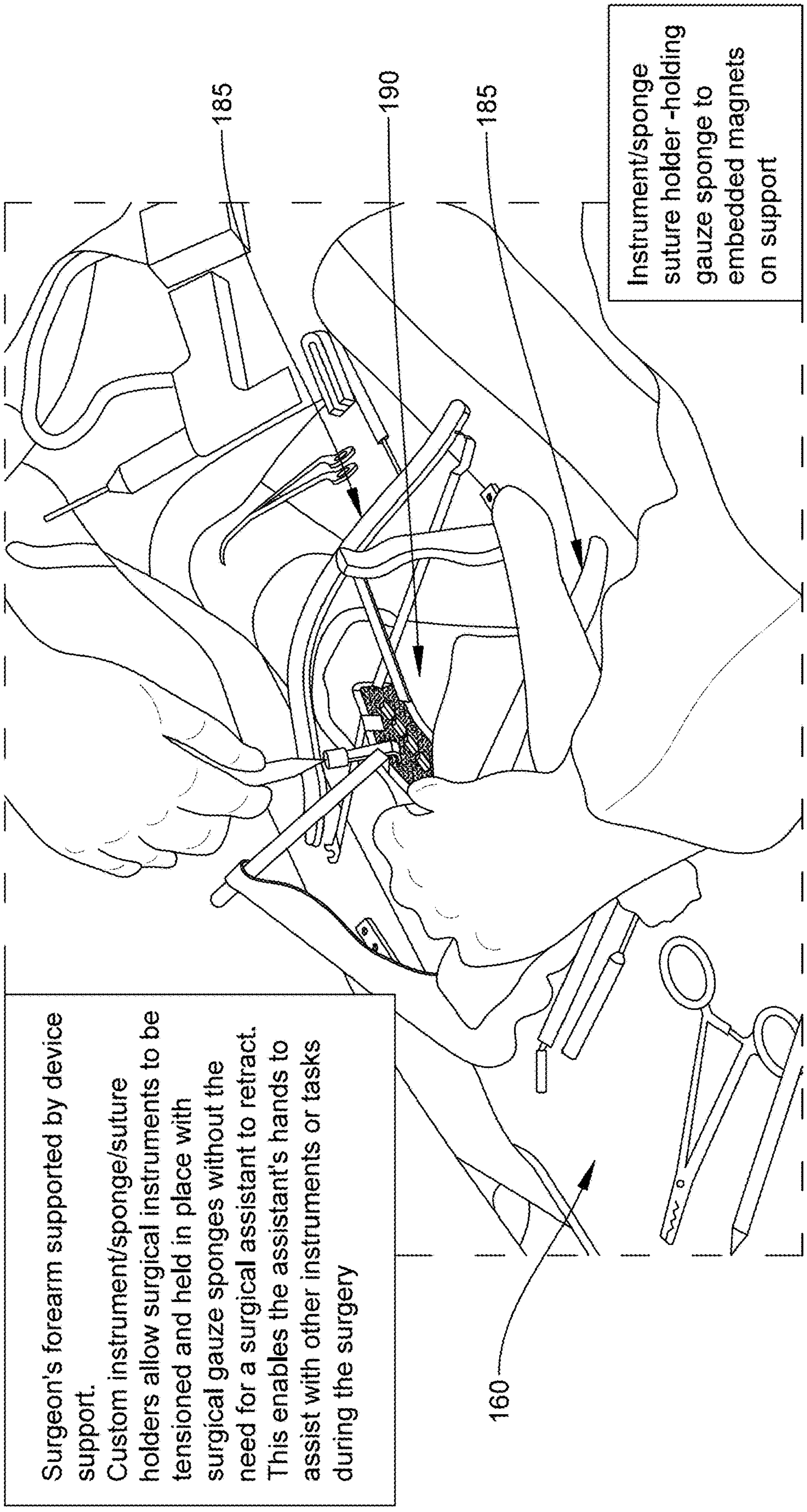
FIG. 9 illustrates a patient's hand secured to the hand table device and a surgeon operating according to the embodiments of the present invention.

FIG. 9 shows a patient's hand 190 secured to the hand table device 100 and a surgeon operating according to the embodiments of the present invention. Slat members 185 hold the hand 190 in place during surgery.

Figure 10:
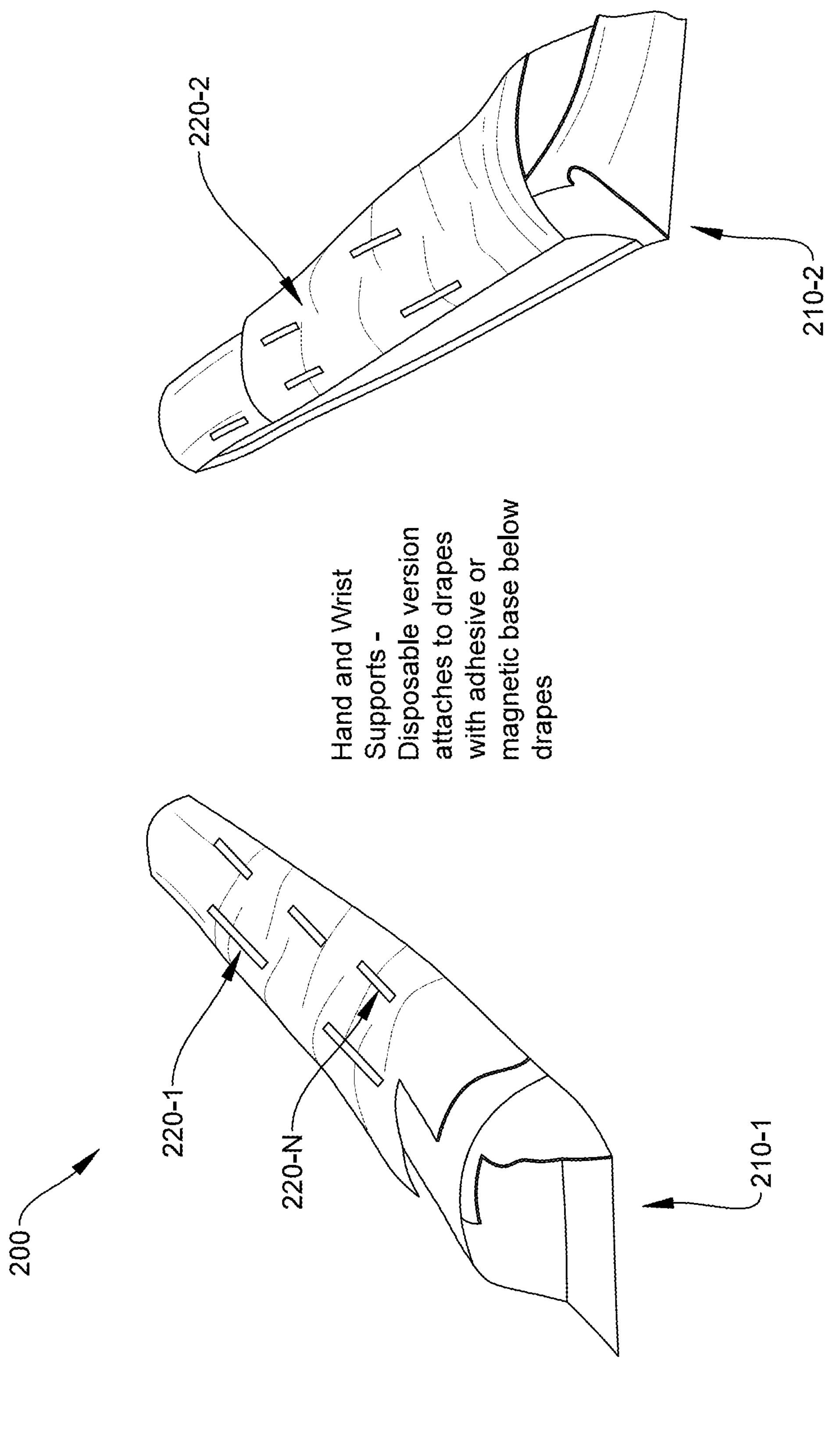
FIG. 10 illustrates a disposable embodiment of a hand table device according to the embodiments of the present invention.

FIG. 10 shows a disposable embodiment of a hand table device 200 according to the embodiments of the present invention. The hand table device 200 comprises two elevated supports 210-1, 210-2 which are secured to the drapes on a hand table. The elevated supports 210-1, 210-2 may be attached to the surgical hand table drapes using magnets attracted to a secure base under the drapes, sterile adhesives (e.g., double-sided tape), hook and loop fasteners and other means or attaches to a surgical drape over the surgical hand table.

To reduce costs, the disposable hand table device 200 utilizes slits/slots 220-1 through 220-N in the elevated supports 210-1, 210-2 to secure magnetic and non-magnetic instruments and medical devices and suture for surgery. By way of example, if the elevated supports 210-1, 210-2 are foam formed, the slits/slots 220-1 through 220-N are created in the foam and covering therefore to accommodate portions of the magnetic and non-magnetic instruments and medical devices to hold them in position.

I claim:

1. A hand table device comprising:

a platform having an elongated raised ridge running a length of substantially all of at least one side thereof, said elongated raised ridge including a planar bottom along a length thereof, said elongated raised ridge raised having a height to serve as a barrier preventing articles from falling off said platform and a hand and forearm support for a user thereof; and one or more integral magnets positioned within said elongated raised ridge to secure magnetic articles including surgical instruments, medical devices and/or clips thereto.

2. The hand table device of claim 1 wherein said elongated raised ridge is removably attached to and re-positionable on said platform.

3. The hand table device of claim 2 further comprising two or more sets of holes for attachment of said elongated raised ridge.

4. The hand table device of claim 1 further comprising a removable elongated raised ridge along each of two spaced sides of said platform.

5. The hand table device of claim 1 wherein said platform is rectangular.

6. The hand table device of claim 5 further comprising a removable elongated raised ridge along each of two long sides of said platform.

7. A hand table device system comprising:

a platform having an elongated raised ridge running a length of substantially all of at least one side thereof, said elongated raised ridge including a planar bottom along a length thereof said elongated raised ridge raised having a height to serve as a barrier preventing articles from falling off said platform and a hand and forearm support for a user thereof;

one or more integral magnets positioned to secure magnetic articles including instruments, medical devices and/or clips thereto; and one or more clips or slats for securing a body part on said platform.

8. The hand table device of claim 7 wherein said elongated raised ridge is removably attached to and re-positionable on said platform.

9. The hand table device of claim 8 further comprising two or more sets of holes for attachment of said elongated raised ridge.

10. The hand table device of claim 7 further comprising a removable elongated raised ridge along each of two spaced sides of said platform.

11. The hand table device of claim 7 wherein said platform is rectangular.

12. The hand table device of claim 11 further comprising a removable elongated raised ridge along each of two long sides of said platform.

13. A disposable hand table device comprising:

one or more independent raised elongated ridges, said one or more independent elongated raised ridges including one or more slots for retaining surgical instruments and medical devices including a planar bottom along a length thereof;

means for securing said one or more independent elongated raised ridges to a surgical table; and wherein said one or more elongated raised ridges have a height to serve as a barrier preventing articles from falling off said surgical table and a hand and forearm support for a user thereof.

14. The disposable hand table device of claim 13 wherein said means includes magnets and adhesives.

* * * * *